United States Patent
Kuntz

(10) Patent No.: US 9,717,824 B2
(45) Date of Patent: Aug. 1, 2017

(54) MULTI-COMPONENT JOINING OF PLASTIC PREPARATIONS IN ORDER TO PRODUCE MEDICAL DEVICES WITH FUNCTIONAL SURFACES

(71) Applicant: CeramTec GmbH, Piochingen (DE)

(72) Inventor: Meinhard Kuntz, Esslingen (DE)

(73) Assignee: CeramTec GmbH, Plochingen (DE)

( * ) Notice: Subject to any disclaimer, the term of this patent is extended or adjusted under 35 U.S.C. 154(b) by 0 days.

(21) Appl. No.: 14/416,986

(22) PCT Filed: Jul. 26, 2013

(86) PCT No.: PCT/EP2013/065810
§ 371 (c)(1),
(2) Date: Jan. 23, 2015

(87) PCT Pub. No.: WO2014/019954
PCT Pub. Date: Feb. 6, 2014

(65) Prior Publication Data
US 2015/0224228 A1    Aug. 13, 2015

(30) Foreign Application Priority Data

Jul. 30, 2012   (DE) .......... 10 2012 213 348

(51) Int. Cl.
| A61F 2/28 | (2006.01) |
| A61L 27/10 | (2006.01) |
| A61L 27/44 | (2006.01) |
| A61L 27/30 | (2006.01) |
| A61L 27/56 | (2006.01) |

(52) U.S. Cl.
CPC .............. *A61L 27/443* (2013.01); *A61F 2/28* (2013.01); *A61L 27/10* (2013.01); *A61L 27/105* (2013.01); *A61L 27/306* (2013.01); *A61L 27/446* (2013.01); *A61L 27/56* (2013.01); *A61F 2310/00179* (2013.01); *A61L 2400/08* (2013.01); *A61L 2420/04* (2013.01); *A61L 2430/02* (2013.01)

(58) Field of Classification Search
None
See application file for complete search history.

(56) References Cited

U.S. PATENT DOCUMENTS

| 4,969,913 | A | 11/1990 | Ojima | |
| 6,302,913 | B1* | 10/2001 | Ripamonti | A61C 8/0012 623/16.11 |
| 2010/0076570 | A1 | 3/2010 | Band et al. | |
| 2010/0137972 | A1 | 6/2010 | Kuntz et al. | |
| 2011/0045279 | A1* | 2/2011 | Heinl | C04B 33/13 428/318.6 |
| 2012/0142237 | A1 | 6/2012 | Kuntz et al. | |
| 2015/0224228 | A1* | 8/2015 | Kuntz | A61L 27/10 623/16.11 |

FOREIGN PATENT DOCUMENTS

| DE | 38 32 942 A1 | 4/1989 |
| DE | 199 45 429 A1 | 4/2001 |
| DE | 10 2007 020 471 A1 | 11/2008 |
| DE | 10 2008 001 402 A1 | 10/2009 |

OTHER PUBLICATIONS

US 6,117,172, 09/2000, Ripamonti et al. (withdrawn)

* cited by examiner

*Primary Examiner* — Peter A Salamon
(74) *Attorney, Agent, or Firm* — Norton Rose Fulbright US LLP; James Crawford

(57) ABSTRACT

A process for producing medical devices with functional surfaces, e.g., ceramic implants having bone-affine surfaces, and to medical devices produced in such a manner.

14 Claims, No Drawings

MULTI-COMPONENT JOINING OF PLASTIC PREPARATIONS IN ORDER TO PRODUCE MEDICAL DEVICES WITH FUNCTIONAL SURFACES

This application is a §371 of International Application No. PCT/EP2013/065810 filed Jul. 26, 2013, and claims priority from German Patent Application No. 10 2012 213 348.8 filed Jul. 30, 2012.

FIELD OF THE INVENTION

The invention relates to a process to produce medical devices with functional surfaces. In particular, the invention relates to a process by which ceramic implants having bone-affine surfaces may be produced and to medical devices produced in such a manner.

BACKGROUND OF THE INVENTION

Structural ceramic components, in particular implants, prostheses, or the like, are currently often applied with a functional coating, e.g. a bone-affine or antiseptic coating or layer. The functional surface is to improve the integration of the component in the body. In particular, a faster and more durable incorporation of the component is often concerned which can be achieved, e.g., by porous coatings or surfaces. Pores on the surface of the component may enable or facilitate the ingrowth of bone components, and therefore enable a secure hold of the implant by the body's own integration. On the other hand, inflammatory processes often also have to be managed, which are often unavoidable when inserting the implant into the body. Components used as a joint replacement generally require a functional layer for connection to the bone.

Such implants, in particular also made from ceramics, are known from the state of the art. They are generally produced in multiple work steps, wherein a functional or porous surface is applied in some way, e.g. by coating, to the base body which is massive and supporting. These production processes are comparatively time-consuming and cumbersome since different processes for forming of the base body and subsequent surface treatment are required.

OBJECTS OF THE INVENTION

Thus, one object of the invention is to provide a process simplifying the production of an implant, e.g. a prosthesis, having a core material and a functional surface material.

The object is achieved by a process according to the process for producing an implant having at least one functional surface of the invention described herein. Advantageous embodiments of the process are described below.

SUMMARY OF THE INVENTION

Therefore, a process of the invention for producing an implant having a functional surface provides for producing a base body and the functional surface in one work step.

DETAILED DESCRIPTION

According to a further development, the invention comprises ceramic components having a massive, supporting area, and having a porous, bone-affine interface or surface, which are produced in one work step.

For the high-performance ceramics to be produced a corresponding powder mixture is prepared, in which both homogenization of the individual aggregates as well as dispersion of the powder agglomerates are implemented according to the state of the art. E.g. zirconia, silicon nitride, alumina or composite materials like ZTA and/or mixtures of said substances may be considered. Additionally, educts may be used that may be reacted to obtain said substances, e.g. by sintering under a specific atmosphere as required. A plastic binder system is added to the powder mixture, thus forming a molding material (feedstock) that allows for molding via high or low pressure injection molding or also by extrusion.

Non-plastic, particulate aggregates (placeholder) may be added to a portion of the feedstock which may, after molding, e.g. during the subsequent sintering process, be removed again mostly residue-free to leave pores. E.g. polyethylene, polystyrene or similar organic carbon compounds or also graphite may be added as aggregates. According to a preferred embodiment of the invention the placeholders are added to the feedstock to leave pores in the body after sintering, the pores being particularly advantageous for the ingrowth characteristic into the bone.

A particularly preferred process for producing implants having at least one functional surface comprises the following steps:

(a) preparation of a ceramic powder mixture;
(b) adding to the ceramic powder mixture a plastic binder system, wherein the plastic binder system is adapted to a subsequent molding process, and the ceramic powder mixture with the plastic binder system forms a first feedstock;
(c1) dividing the first feedstock and adding aggregates to a part of the feedstock to form a second feedstock; or
(c2) producing a second feedstock according to steps (a) and (b);
(d) carrying out a molding process in which the base body and the bone-affine surface are being molded from the first and second feedstocks;
(e) debinding of the green part;
(f) sintering and debinding the brown part of the implant molded in the previous step to yield the finished implant having a functional and particularly a bone-affine surface.

According to a particularly preferred embodiment of the invention, first and second feedstocks may be produced and processed both with and without placeholders/aggregates as follows:

The feedstocks with and without placeholder each may be used separately for molding by injection molding and/or extrusion, respectively.

During the molding process the feedstocks may be brought in contact with each other under controlled conditions. The chosen organic binder system enables adhesion bonding of the plastic materials. The molding process typically is heat-activated at temperatures from 80° C. to 170° C.

The feedstocks are set so that they can be sintered under the same conditions and that they have a similar sintering kinetics so as to retain the bonding of the massive feedstock with the placeholder-containing feedstock during sintering and to generate a solid body connection by sintering.

The two feedstocks are processed via two-component injection molding or two-component extrusion and thereby are given the desired shape. According to the invention, the later massive, supporting areas of the component with the massive feedstock and the porous, bone-affine areas are filled by the aggregate/placeholder-containing feedstock via multi-component molding. Thereby, within the limits of these two processes, any molded padding may be produced by which the objective of massive solid bodies having bone-affine, porous surfaces may be arbitrarily realized. Depending on the application, e.g. spacers for spine implants, the porous area may also occupy larger areas or continuous ducts of the component.

After thermally activated molding and subsequent cooling a relatively stable green part containing the ceramic powder, the organic plasticizer and the placeholders is generated. The plasticizers are being removed, e.g., via evaporation or acid washing.

The debinded green part (brown part) is sintered generating the desired massive and porous areas according to the invention. The placeholders are cauterized. The transition region between massive and porous ceramics is hardened by the sintering process.

It is claimed:

1. A process for producing an implant having a functional surface, wherein a base body and the functional surface are produced in one work step; wherein the process comprises the steps of:
   (a) preparation of a ceramic powder mixture;
   (b) adding to the ceramic powder mixture a plastic binder system, wherein the plastic binder system is adapted to a subsequent molding process, and the ceramic powder mixture with the plastic binder system forms a first feedstock;
   (c) dividing the first feedstock and adding aggregates to a part of the feedstock to form a second feedstock;
   (d) carrying out a molding process, wherein the base body and the bone-affine surface are molded from the first and second feedstock, wherein the molding process is a high or low pressure injection molding process or an extrusion process
   (e) debinding of the green part;
   (f) sintering and debinding of the brown part of the implant molded in the previous step to yield the finished implant with a bone-affine surface.

2. The process according to claim 1, wherein the functional surface is a bone-affine surface.

3. The process according to claim 1, wherein a ceramic powder is used as base material.

4. The process according to claim 3, wherein the ceramic powder comprises at least one member selected from the group consisting of zirconia, silicon nitride, alumina, and ZTA.

5. The process according to claim 1, wherein the base body and the material of the bone-affine surface are produced from the same base material.

6. The process according to claim 1, wherein the base body and the material of the bone-affine surface comprise a plastic binder system enabling adhesion bonding between the base body and the material of the bone-affine surface after curing, the plastic binder system preferably being an organic binder system.

7. The process according to claim 1, further comprising the step of adding aggregates to a part of the base material serving as the basis for the material of the bone-affine surface, and removed again after molding, thereby adjusting a defined porosity of the bone-affine surface.

8. The process according to claim 7, wherein the aggregates are particulate and comprise at least one member selected from the group consisting of polyethylene, polystyrene, graphite and an organic carbon compound.

9. The process according to claim 2, further comprising the step of adding aggregates to a part of the base material serving as the basis for the material of the bone-affine surface, and removed again after molding, thereby adjusting a defined porosity of the bone-affine surface.

10. The process according to claim 1, wherein injection molding is two-component injection molding or wherein the extrusion is two-component extrusion.

11. The process according to claim 10, wherein the molding process is thermally activated, preferably at temperatures from 80° C. to 170° C.

12. The process according to claim 9, wherein feedstocks are composed so as to enable being sintered under the same conditions.

13. An implant prepared by the process of claim 1.

14. The process according to claim 3, wherein the ceramic powder comprises at least one member selected from the group consisting of zirconia, silicon nitride and alumina.

* * * * *

UNITED STATES PATENT AND TRADEMARK OFFICE
CERTIFICATE OF CORRECTION

PATENT NO. : 9,717,824 B2
APPLICATION NO. : 14/416986
DATED : August 1, 2017
INVENTOR(S) : Meinhard Kuntz It is certified that error appears in the above-identified patent and that said Letters Patent is hereby corrected as shown below:

On the Title Page

Item (75) Inventor change:
"Meinhard Kuntz, Esslingen"
To:
--Meinhard Kuntz, Esslingen,
Moritz Messmer, Stuttgart,
Simon Heinzmann, Geislingen/Aufhausen--

Signed and Sealed this
Twenty-ninth Day of January, 2019

Andrei Iancu
*Director of the United States Patent and Trademark Office*